United States Patent
Chen

(10) Patent No.: US 11,127,291 B2
(45) Date of Patent: Sep. 21, 2021

(54) VEHICLE WARNING METHOD, TELEMATICS CONTROL UNIT AND DEVICE BASED ON VEHICLE-TO-EVERYTHING (V2X) COMMUNICATIONS

(71) Applicant: Wistron NeWeb Corp., Hsinchu (TW)

(72) Inventor: Tsu-Shou Chen, Hsinchu (TW)

(73) Assignee: WISTRON NEWEB CORP., Hsinchu (TW)

( * ) Notice: Subject to any disclaimer, the term of this patent is extended or adjusted under 35 U.S.C. 154(b) by 0 days.

(21) Appl. No.: 17/086,572

(22) Filed: Nov. 2, 2020

(65) Prior Publication Data
US 2021/0166557 A1 Jun. 3, 2021

(30) Foreign Application Priority Data
Nov. 28, 2019 (TW) ................................ 108143364

(51) Int. Cl.
| | | |
|---|---|---|
| G08B 1/00 | (2006.01) |
| G08G 1/09 | (2006.01) |
| H04W 4/40 | (2018.01) |
| A61B 5/00 | (2006.01) |
| A61B 5/024 | (2006.01) |
| G07C 5/02 | (2006.01) |

(52) U.S. Cl.
CPC ............ *G08G 1/091* (2013.01); *A61B 5/024* (2013.01); *A61B 5/6893* (2013.01); *A61B 5/746* (2013.01); *H04W 4/40* (2018.02); *G07C 5/02* (2013.01)

(58) Field of Classification Search
CPC ...... G08G 1/091; A61B 5/6893; A61B 5/746; A61B 5/024; H04W 4/40; G07C 5/02; B60W 60/00; B60W 40/08; B60W 60/0059; B60W 60/001; B60W 60/0051; B60W 60/0055; G06N 20/00
See application file for complete search history.

(56) References Cited

U.S. PATENT DOCUMENTS

| | | | | |
|---|---|---|---|---|
| 10,561,357 B2* | 2/2020 | Patel | .................... | G07C 5/0825 |
| 10,796,175 B2* | 10/2020 | Shimizu | ................. | G08B 21/06 |
| 2013/0009761 A1* | 1/2013 | Horseman | ............... | A61B 5/18 |
| | | | | 340/425.5 |
| 2020/0269849 A1* | 8/2020 | Kang | .................... | B60W 50/14 |
| 2021/0031807 A1* | 2/2021 | Yamamoto | ........... | G05D 1/0061 |

FOREIGN PATENT DOCUMENTS

CN 106585624 B 7/2019

* cited by examiner

*Primary Examiner* — Toan N Pham
(74) *Attorney, Agent, or Firm* — McClure, Qualey & Rodack, LLP

(57) ABSTRACT

A vehicle warning method based on Vehicle-to-everything (V2X) communication is provided. The method is used in a telematics control unit (TCU) installed in a first vehicle and includes: receiving a heartbeat frequency of a user driving the first vehicle; determining whether the heartbeat frequency is within a normal range; adding a first loss-of-control flag into a first basic safety message (BSM) when the heartbeat frequency is not within the normal range; and broadcasting the first BSM.

14 Claims, 9 Drawing Sheets

| | Data frames | Description | Remarks |
|---|---|---|---|
| Part I | DSRCmsgID | | |
| Part I: BSM Blob (Octet string) | MsgCnt | | |
| | TemporatyID | | |
| | Dsecond | | |
| | Latitude | | |
| | Longitude | | |
| | Elevation | | |
| | PositionalAccuracy | | |
| | TransmissionAndSpeed | | |
| | AccelerationSet4Way | | |
| | BrakeSystemStatus | | |
| | VehicleSize | | |
| Part II | SafetyExtension | | Optional |
| | VehicleStatus | | Optional |

| Data item | Detail | Remarks |
|---|---|---|
| DF_SafetyExtension | EventFlag | |
| | PathHistory | |
| | PathPrediction | |
| | RTCMPackage | |
| | LossOfControl | |

FIG. 5

VEHICLE WARNING METHOD, TELEMATICS CONTROL UNIT AND DEVICE BASED ON VEHICLE-TO-EVERYTHING (V2X) COMMUNICATIONS

CROSS REFERENCE TO RELATED APPLICATIONS

This application claims priority from Taiwan Patent Application No. 108143364, filed on Nov. 28, 2019, the disclosure of which is incorporated herein by reference in its entirety.

BACKGROUND

Technical Field

The present disclosure generally relates to a method, telematics control unit (TCU) and device based on Vehicle-to-everything (V2X) communication. More specifically, aspects of the present disclosure relate to a vehicle warning method, a telematics control unit, and a device based on V2X communication.

Description of the Related Art

Vehicle-to-everything communication refers to providing vehicle information via sensors, onboard terminals, and electronic tags mounted on a vehicle, implementing interconnection and intercommunication of Vehicle to Vehicle (V2V), Vehicle to Network (V2N), Vehicle to Infrastructure (V2I), and Vehicle to Pedestrian (V2P) using various communication technologies, extracting and sharing information on an information network platform for effective use, and effectively controlling the vehicles, and providing comprehensive services. FIG. 1 is a schematic diagram of V2V, V2N, V2I and V2P in the related art.

It is not unknown for vehicle drivers (especially drivers of a large vehicles) to die suddenly while at the wheel. This has the inherent risk of harming other drivers in other vehicles and pedestrians on the same road or highway. In the past, there was no effective method to detect the heart condition of car drivers and effectively notify other drivers and pedestrians.

Therefore, there is a need for a vehicle warning method, a telematics control unit, and a device based on V2X communication to solve this problem.

SUMMARY

The following summary is illustrative only and is not intended to be limiting in any way. That is, the following summary is provided to introduce concepts, highlights, benefits and advantages of the novel and non-obvious techniques described herein. Select, not all, implementations are described further in the detailed description below. Thus, the following summary is not intended to identify essential features of the claimed subject matter, nor is it intended for use in determining the scope of the claimed subject matter.

Therefore, the main purpose of the present disclosure is to provide a vehicle warning method, telematics control unit and device based on V2X communication to overcome the above disadvantages.

In an exemplary embodiment, a vehicle warning method based on Vehicle-to-everything (V2X) communication, used in a telematics control unit (TCU) installed in a first vehicle, comprising: receiving a heartbeat frequency of a user driving the first vehicle; determining whether the heartbeat frequency is within a normal range; adding a first loss-of-control flag into a first basic safety message (BSM) when the heartbeat frequency is not within the normal range; and broadcasting the first BSM.

In some embodiments, the first loss-of-control flag is located in a first safety extension frame in the first BSM.

In some embodiments, the method further comprises: receiving a second BSM; determining whether the second BSM comprises a second loss-of-control flag; and transmitting a warning message to notify the user when the second BSM comprises the second loss-of-control flag.

In some embodiments, before transmitting the warning message to notify the user, the method further comprises: obtaining second vehicle information in the second BSM; predicting a track of the second vehicle based on the second vehicle information; determining whether the first vehicle is located in a critical area according to the track; and transmitting the warning message to notify the user when the first vehicle is located in the critical area.

In some embodiments, the second vehicle information comprises at least a position, a speed, a braking state, and a size of a second vehicle.

In some embodiments, the second loss-of-control flag is located in a second safety extension frame in the second BSM.

In an exemplary embodiment, a telematics control unit (TCU) based on Vehicle-to-everything (V2X) communication, installed in a vehicle, comprising: one or more processors; and one or more computer storage media for storing one or more computer-readable instructions, wherein the processor is configured to drive the computer storage media to execute the following tasks: receiving a heartbeat frequency of a user driving the vehicle; determining whether the heartbeat frequency is within a normal range; adding a loss-of-control flag into a basic safety message (BSM) when the heartbeat frequency is not within the normal range; and broadcasting the BSM.

In an exemplary embodiment, vehicle warning device based on Vehicle-to-everything (V2X) communication, comprising: one or more processors; and one or more computer storage media for storing one or more computer-readable instructions, wherein the processor is configured to drive the computer storage media to execute the following tasks: receiving a basic safety message (BSM); determining whether the BSM comprises a loss-of-control flag; and transmitting a warning message to notify a user when the BSM comprises the loss-of-control flag.

BRIEF DESCRIPTION OF DRAWINGS

The accompanying drawings are included to provide a further understanding of the disclosure, and are incorporated in and constitute a part of the present disclosure. The drawings illustrate implementations of the disclosure and, together with the description, serve to explain the principles of the disclosure. It should be appreciated that the drawings are not necessarily to scale as some components may be shown out of proportion to their size in actual implementation in order to clearly illustrate the concept of the present disclosure.

FIG. 5 is a table illustrating the BSM and the security extension frame according to an embodiment of the present disclosure.

DETAILED DESCRIPTION

Various aspects of the disclosure are described more fully below with reference to the accompanying drawings. This disclosure may, however, be embodied in many different forms and should not be construed as limited to any specific structure or function presented throughout this disclosure. Rather, these aspects are provided so that this disclosure will be thorough and complete, and will fully convey the scope of the disclosure to those skilled in the art. Based on the teachings herein one skilled in the art should appreciate that the scope of the disclosure is intended to cover any aspect of the disclosure disclosed herein, whether implemented independently of or combined with any other aspect of the disclosure. For example, an apparatus may be implemented or a method may be practiced using number of the aspects set forth herein. In addition, the scope of the disclosure is intended to cover such an apparatus or method which is practiced using another structure, functionality, or structure and functionality in addition to or other than the various aspects of the disclosure set forth herein. It should be understood that any aspect of the disclosure disclosed herein may be embodied by one or more elements of a claim.

The word "exemplary" is used herein to mean "serving as an example, instance, or illustration." Any aspect described herein as "exemplary" is not necessarily to be construed as preferred or advantageous over other aspects. Furthermore, like numerals refer to like elements throughout the several views, and the articles "a" and "the" includes plural references, unless otherwise specified in the description.

It should be understood that when an element is referred to as being "connected" or "coupled" to another element, it may be directly connected or coupled to the other element or intervening elements may be present. In contrast, when an element is referred to as being "directly connected" or "directly coupled" to another element, there are no intervening elements present. Other words used to describe the relationship between elements should be interpreted in a like fashion. (e.g., "between" versus "directly between", "adjacent" versus "directly adjacent", etc.).

The present disclosure provides a vehicle warning method, telematics control unit and device based on V2X communication, which can be applied to a vehicle security system, based on V2X communication, and may utilize the information exchange between the telematics control units (TCUs) of the vehicles and the mobile devices of drivers and pedestrians to achieve the purpose of notifying specific drivers and pedestrians, so as to further assist the security of driving and pedestrians.

Figure 1:
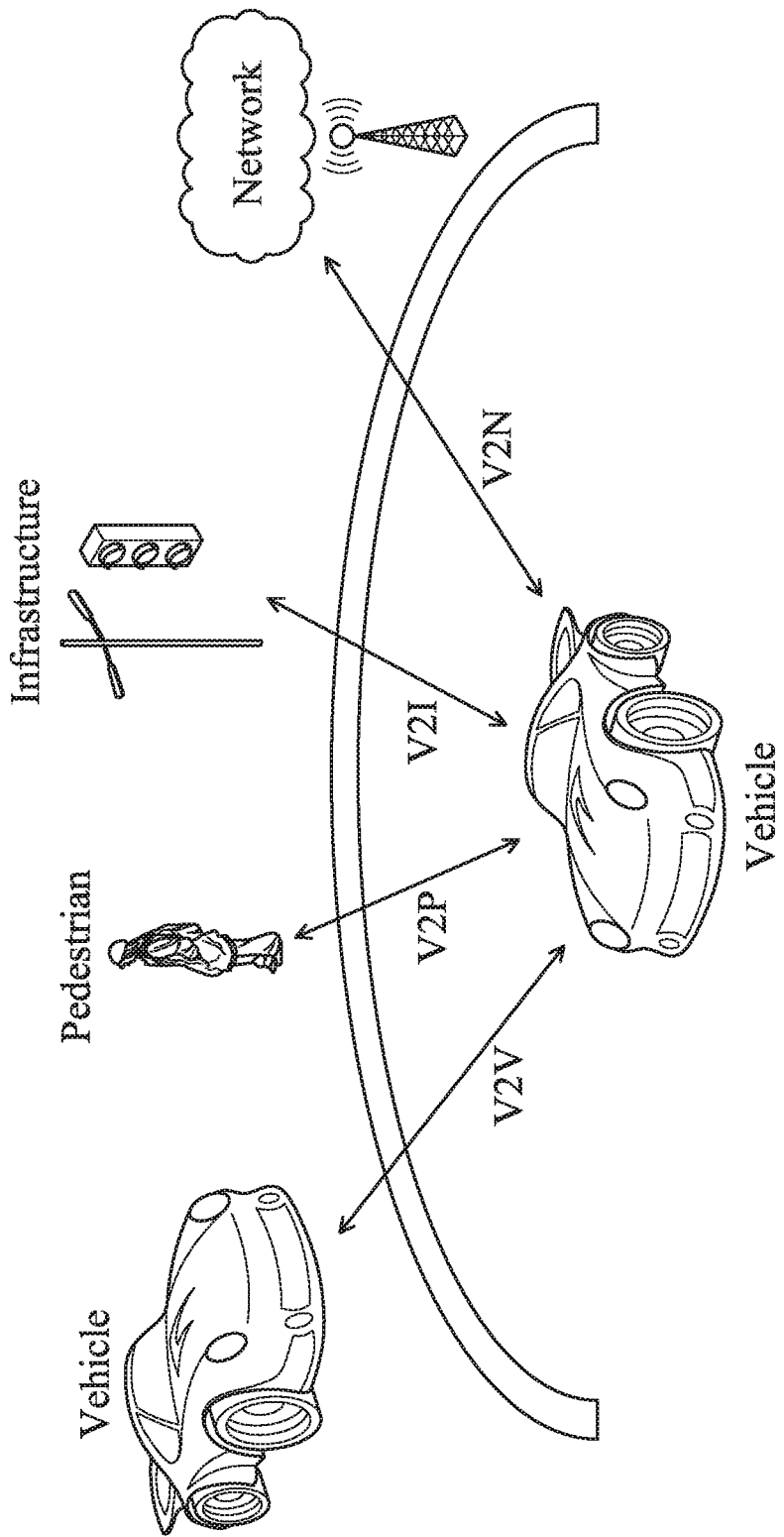
FIG. 1 is a schematic diagram of V2V, V2N, V2I and V2P in the related art.
Figure 2:
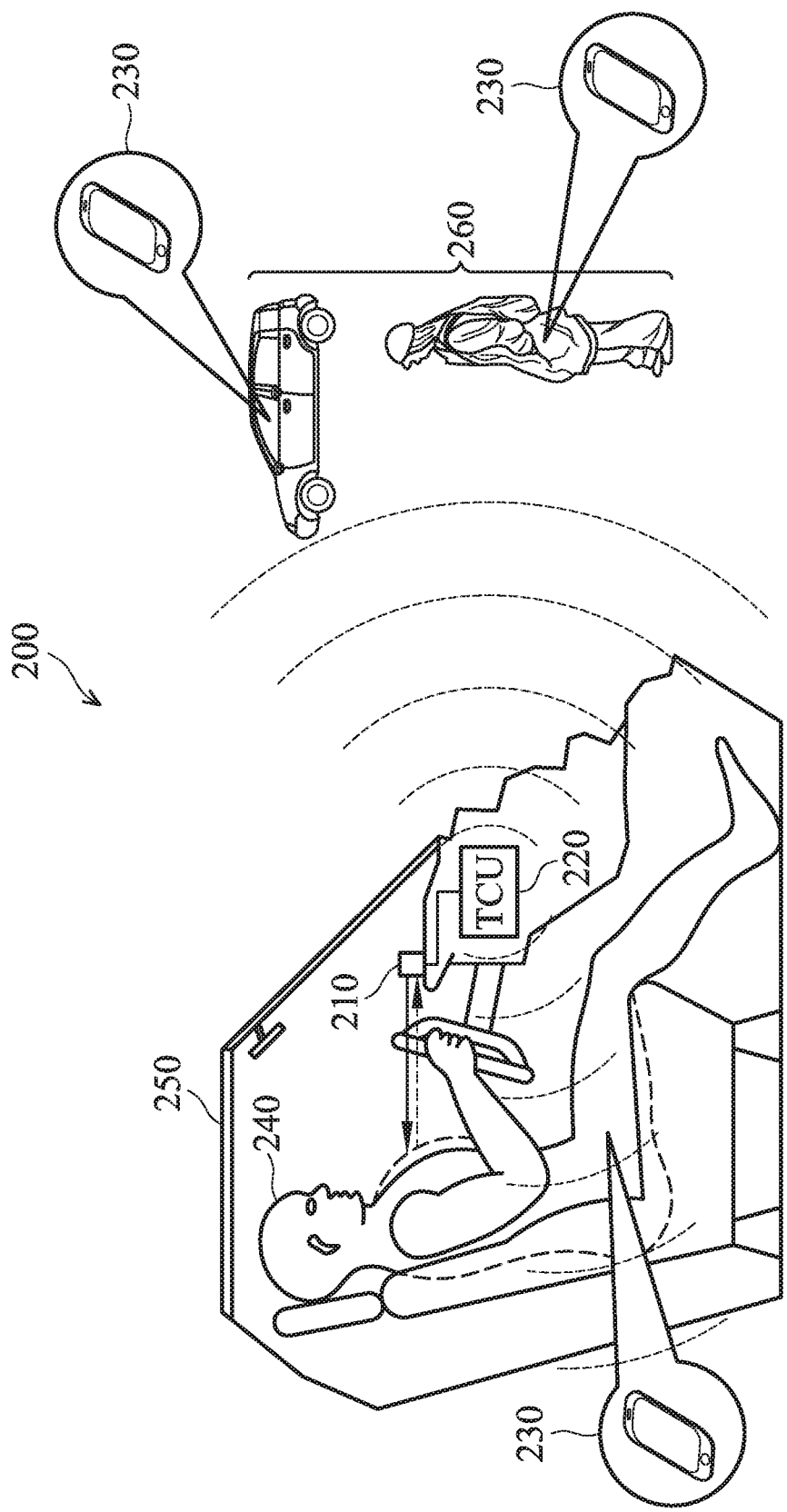
FIG. 2 is a schematic diagram illustrating a vehicle warning system based on V2X communication according to an embodiment of the present disclosure.

FIG. 2 is a schematic diagram illustrating a vehicle warning system 200 based on V2X communication according to an embodiment of the disclosure. Specifically, the vehicle warning system 200 comprises a radar device 210 that is installed in a vehicle 250 and used for detecting a heart rate, a Telematics Control Unit (TCU) 220 and a mobile device 230. The radar device 210 for detecting the heart rate is placed adjacent to the user 240 driving the vehicle 250, wherein the distance between the radar device 210 and the user 240 is, for example, about 30-90 cm.

Figure 3:
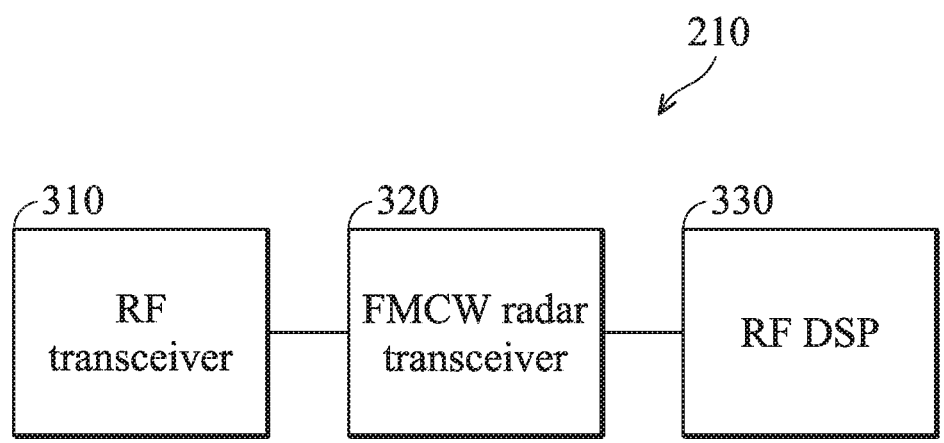
FIG. 3 is a simplified functional block diagram illustrating a radar device according to an embodiment of the present disclosure.

The radar device 210 may include at least a radio frequency (RF) transceiver 310, a frequency-modulated continuous-wave (FMCW) radar transceiver 320, and a RF digital signal processor (DSP) 330, as shown in FIG. 3. The RF DSP 330 can transmit the radar measurement signal 20 times per second drove by the FMCW radar transceiver 320 to the chest of the user 240. The RF transceiver 310 may receive the radar reflection signal reflected the radar measurement signal through the user 240, and may transmit the radar reflection signal to the RF DSP 330 through the FMCW radar transceiver 320. Since the radar device 210 is very sensitive to changes in the distance of more than 1 cm, the RF DSP 330 may capture each reflected wave in the radar reflected signal and calculate the heartbeat rate and the respiratory rate through Fast Fourier Transform (FFT), phase capture and analysis and processing based on the changes in the displacement of the chest of the user 240 during breathing.

The TCU 220 can periodically (for example, 10 seconds) read the heartbeat frequency of the user 240 calculated by the RF DSP 330 in the radar device 210 through a hardware connection interface. The TCU 220 may define a normal range of the heartbeat frequency in advance. When the TCU 220 detects that the heartbeat frequency of the user 240 is not within a normal range, the TCU 220 continuously monitors the heartbeat frequency of the user 240 for a period of time. When the heartbeat frequency of the user 240 does not return to the normal range, the TCU 220 may broadcast a V2X packet comprising hazard information of the user 240 to notify the drivers driving the vehicles and the pedestrians 260 around the vehicle 250.

The mobile device 230 may be used by the user 240 driving the vehicle 250 or the drivers driving the vehicles and the pedestrians 260 around the vehicle 250. The mobile device 230 may support various wireless access technologies, and the mobile device 230 may be an electronic device, such as a mobile phone, a notebook computer, a smart phone, or a tablet computer. The mobile device 230 may at least comprise a communication device and a processor (not shown in the FIG. 2) for performing wireless transmission with the TCU 220 in the vehicle 250. The mobile device 230 may perform wired communication and/or wireless communication for voice and/or data services through the network, wherein the wireless communication between the mobile device 230 and the network, satellite signal capture or V2X may be in compliance with various wireless technologies, such as the Global System for Mobile communications (GSM) technology, General Packet Radio Service (GPRS) technology, Enhanced Data rates for Global Evolution (EDGE) technology, Wideband Code Division Multiple Access (WCDMA) technology, Code Division Multiple Access 2000 (CDMA 2000) technology, Time Division-Synchronous Code Division Multiple Access (TD-SCDMA) technology, Worldwide Interoperability for Microwave Access (WiMAX) technology, Long Term Evolution (LTE) technology, Long Term Evolution Advanced (LTE-A) technology, Global Navigation Satellite System (GNSS) technology, Vehicle to Everything (V2X) technology and others.

Figure 9:
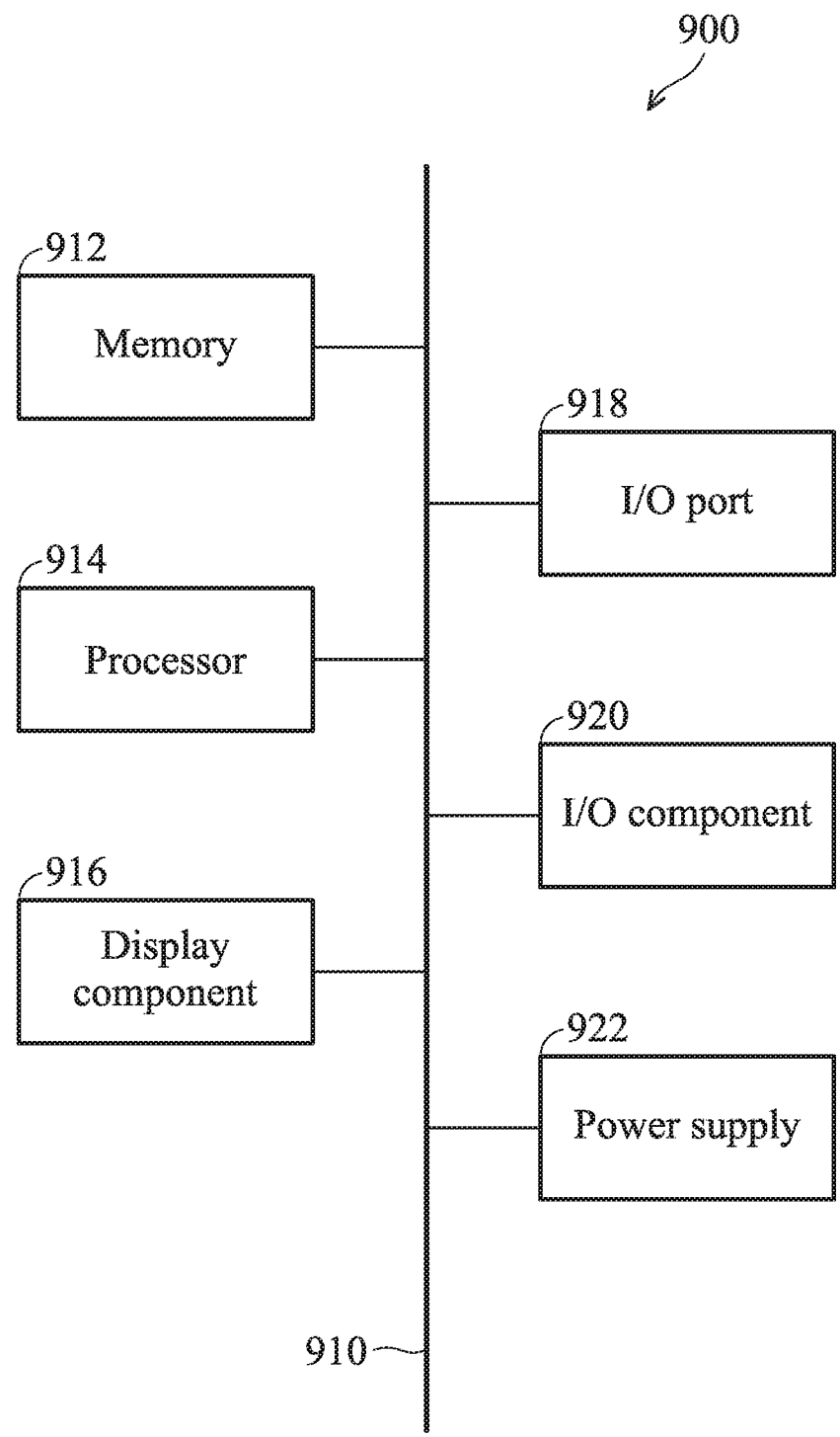
FIG. 9 illustrates an exemplary operating environment for implementing embodiments of the present disclosure.

It should be understood that the TCU 220 and the mobile device 230 shown in FIG. 2 is an example of one suitable vehicle warning system 200 based on V2X communication architecture. The TCU 220 and the mobile device 230 shown in FIG. 2 can be implemented via any type of computing device, such as the computing device 900 described with reference to FIG. 9, as shown in FIG. 9.

Figure 4:
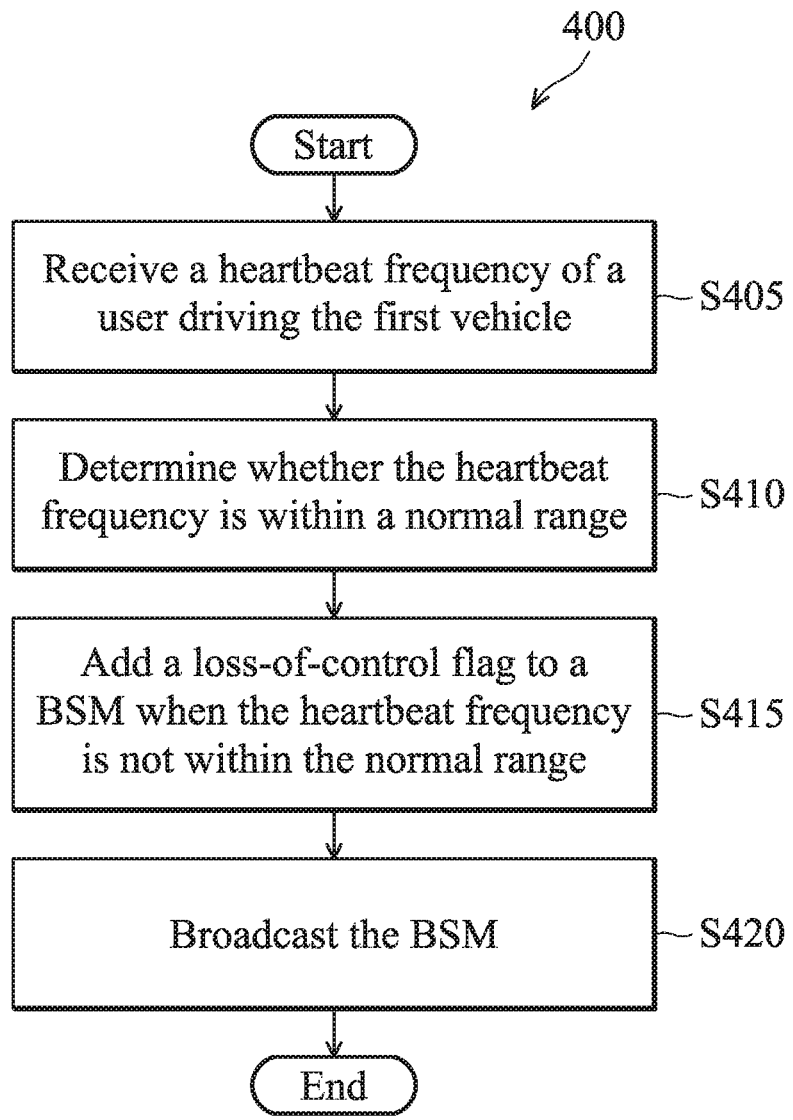
FIG. 4 is a flowchart illustrating a vehicle warning method based on V2X communication according to an embodiment of the present disclosure.

FIG. 4 is a flowchart illustrating a vehicle warning method 400 based on V2X communication according to an embodiment of the present disclosure. The method may be implemented in the TCU 220 installed in the vehicle 250 of the vehicle warning system 200 based on V2X communication as shown in FIG. 2.

In step S405, the TCU receives a heartbeat frequency of a user driving the first vehicle, wherein the heartbeat frequency is transmitted by a radar device. In an embodiment, the TCU may receive the heartbeat frequency transmitted by the radar device in a fixed period (for example, every 10 seconds). Then, in step S410, the TCU determines whether the heartbeat frequency is within a normal range, wherein the normal range is defined in advance by the TCU.

Next, in step S415, when the heartbeat frequency is not within the normal range, the TCU adds a loss-of-control flag to a basic safety message (BSM), wherein the loss-of-control flag is located in a safety extension frame in the BSM. Specifically, FIG. 5 is a table illustrating the BSM 510 and the security extension frame 520 according to an embodiment of the present disclosure. As shown in the table, the second part (Part II) of the BSM 510 may comprise a safety extension (SafetyExtension) frame 520. The loss of control (LossOfControl) flag 512 may be added to the detail frame of the safety extension frame 520, as shown in the FIG. 5. Finally, in step S420, the TCU broadcasts the BSM. In one embodiment, the TCU broadcasts the BSM at a fixed frequency (for example, every 100 milliseconds).

Figure 6:
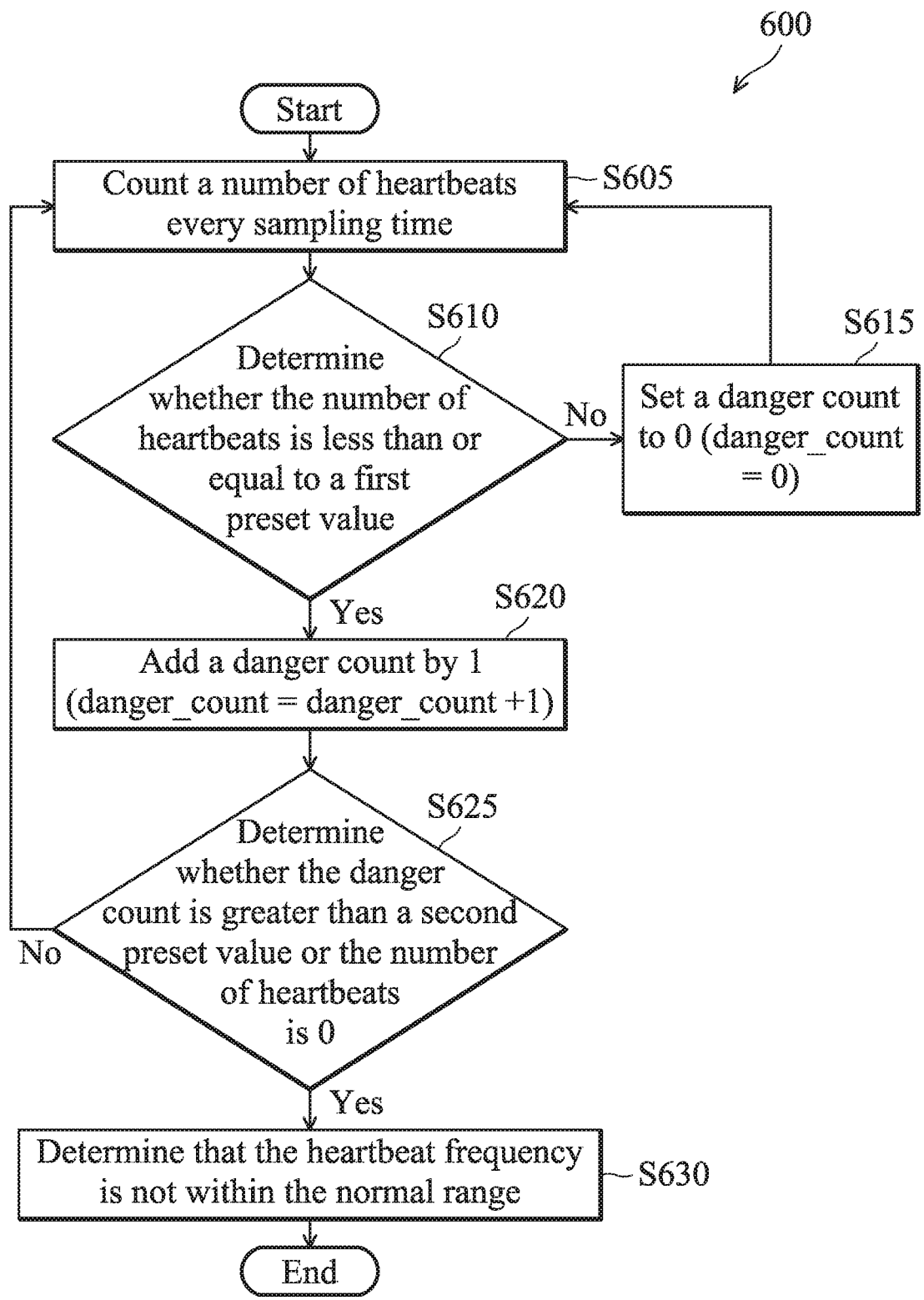
FIG. 6 is a flowchart illustrating how the TCU determines whether the heartbeat frequency is within a normal range according to an embodiment of the present disclosure.

The following will describe in detail how the TCU determines whether the heartbeat frequency is within a normal range in step S410. FIG. 6 is a flowchart 600 illustrating how the TCU determines whether the heartbeat frequency is within a normal range according to an embodiment of the present disclosure.

Before the process starts, the TCU continuously receives the heartbeat frequency transmitted by the radar device. In step S605, the TCU counts a number of heartbeats every sampling time (for example, every 10 seconds). In step S610, the TCU determines whether the number of heartbeats is less than or equal to a first preset value (for example, 5). When the number of heartbeats is not less than or equal to the first preset value ("No" in step S610), in step S615, the TCU sets a danger count to 0 (i.e., danger_count=0), and the process returns to step S605.

When the number of heartbeats is less than or equal to the first preset value ("Yes" in step S610), in step S620, the TCU adds a danger count by 1 (i.e., danger_count=danger_count+1). In step S625, the TCU determines whether the danger count is greater than a second preset value (for example, 5) or the number of heartbeats is 0. When the danger count is not greater than the second preset value or the number of heartbeats is not 0 ("No" in step S625), the process returns to step S605.

When the danger count is greater than the second preset value or the number of heartbeats is 0 ("Yes" in step S625), in step S630, the TCU determines that the heartbeat frequency is not within the normal range.

Figure 7:
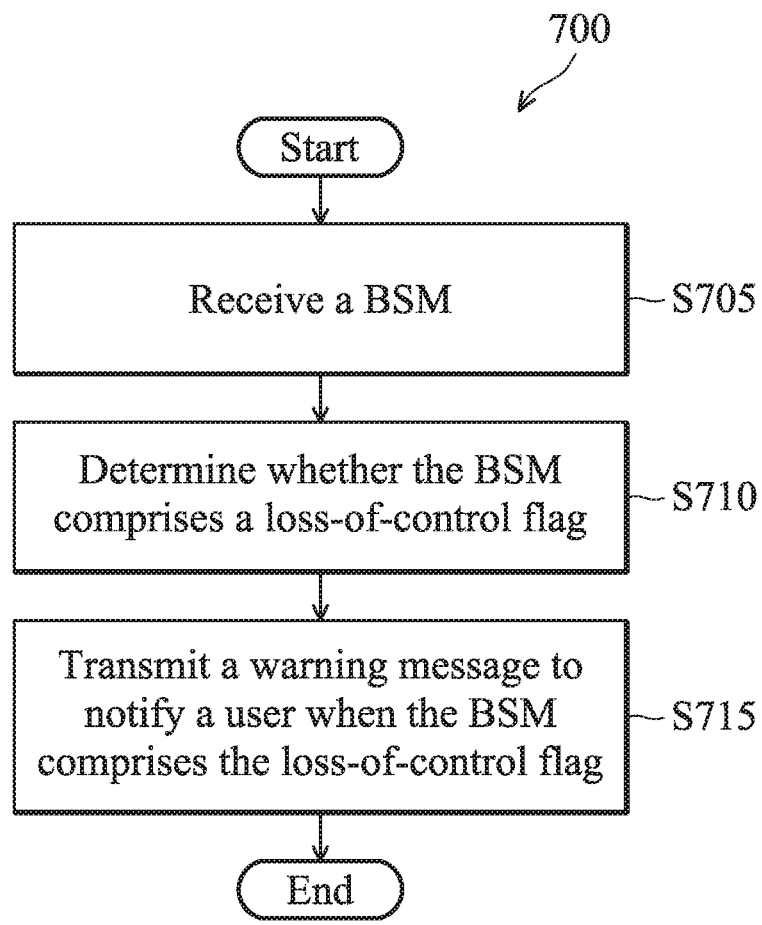
FIG. 7 is a flowchart illustrating a vehicle warning method 700 based on Vehicle-to-everything communication according to an embodiment of the present disclosure.

FIG. 7 is a flowchart illustrating a vehicle warning method 700 based on Vehicle-to-everything communication according to an embodiment of the present disclosure. This method can be implemented in the TCU 220 installed in the vehicle 250 in the vehicle warning system 200 based on Vehicle-to-everything communication as shown in FIG. 2, or be implemented in the mobile device 230 used by the user 240 driving the vehicle 250 or the mobile device 230 used by the drivers driving the vehicles and the pedestrians 260 around the vehicle 250.

In step S705, the device receives a BSM. In step S710, the device determines whether the BSM comprises a loss-of-control flag, wherein the loss-of-control flag is located in a safety extension frame in the BSM. In step S715, when the BSM comprises the loss-of-control flag, the device transmits a warning message to notify a user, wherein the device may use related user interfaces (such as light-emitting diodes (LED), a liquid-crystal display (LCD), a microphone, a buzzer, or Bluetooth streaming) to remind the user that the vehicle broadcasting the BSM is dangerous.

Figure 8:
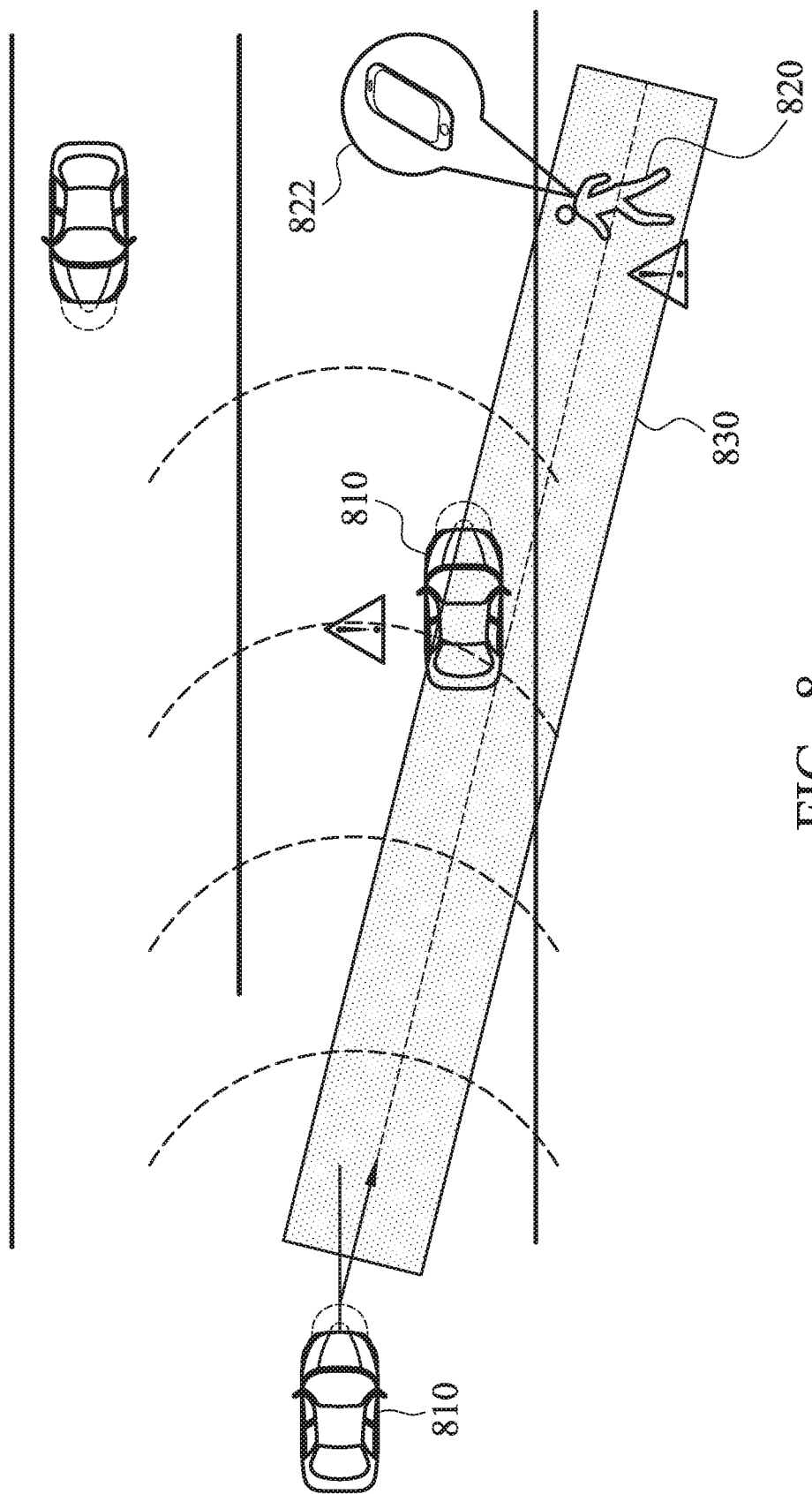
FIG. 8 is a schematic diagram illustrating the critical area where the dangerous vehicle passes by according to an embodiment of the present disclosure.

In one embodiment, before the device transmits the warning message to notify the user, the device may first determine whether the user is located in a critical area passed by the dangerous vehicle broadcasting the BSM. The device may first obtain dangerous vehicle information from the BSM, wherein the dangerous vehicle information comprises at least a position, speed, braking state, and size of the dangerous vehicle. Then, the device predicts the track of the dangerous vehicle based on the dangerous vehicle information. The device may determine whether the device is located in a critical area according to the track. FIG. 8 is a schematic diagram illustrating the critical area where the dangerous vehicle passes by according to an embodiment of the present disclosure. As shown in FIG. 8, the device 822 may obtain information about the location of the user 820 carrying the device 822, to determine whether the user 820 carrying the device 822 is located in the critical area 830 where the dangerous vehicle 810 will pass. When the user 820 is located in the critical area 830, the device 822 may transmit a warning message to notify the user 820, wherein the device 822 may use related user interfaces (such as light-emitting diodes (LED), liquid-crystal displays (LCD), microphones, Buzzer, Bluetooth streaming) to remind the user 820.

As mentioned above, the vehicle warning method, telematics control unit and device based on V2X communication disclosed in the present disclosure may let passengers, external vehicles, or pedestrians know the dangerous information of the driver driving the dangerous vehicle in the shortest time by adding a loss-of-control flag to the BSM and perform corresponding actions, so as to achieve the purpose of reducing casualties.

Having described embodiments of the present disclosure, an exemplary operating environment in which embodiments of the present disclosure may be implemented is described below. Referring to FIG. 9, an exemplary operating environment for implementing embodiments of the present disclosure is shown and generally known as a computing device 900. The computing device 900 is merely an example of a suitable computing environment and is not intended to limit the scope of use or functionality of the disclosure. Neither should the computing device 900 be interpreted as having any dependency or requirement relating to any one or combination of components illustrated.

The disclosure may be realized by means of the computer code or machine-useable instructions, including computer-executable instructions such as program modules, being executed by a computer or other machine, such as a personal data assistant (PDA) or other handheld device. Generally, program modules may include routines, programs, objects, components, data structures, etc., and refer to code that performs particular tasks or implements particular abstract data types. The disclosure may be implemented in a variety of system configurations, including hand-held devices, consumer electronics, general-purpose computers, more specialty computing devices, etc. The disclosure may also be implemented in distributed computing environments where tasks are performed by remote-processing devices that are linked by a communication network.

With reference to FIG. 9, the computing device 900 may include a bus 910 that is directly or indirectly coupled to the following devices: one or more memories 912, one or more processors 914, one or more display components 916, one or more input/output (I/O) ports 918, one or more input/output components 920, and an illustrative power supply 922. The bus 910 may represent one or more kinds of busses (such as an address bus, data bus, or any combination thereof). Although the various blocks of FIG. 9 are shown with lines for the sake of clarity, and in reality, the boundaries of the various components are not specific. For example, the display component such as a display device may be considered an I/O component and the processor may include a memory.

The computing device 900 typically includes a variety of computer-readable media. The computer-readable media can be any available media that can be accessed by computing device 900 and includes both volatile and nonvolatile media, removable and non-removable media. By way of example, not limitation, computer-readable media may comprise computer storage media and communication media. The computer storage media may include volatile and non-volatile, removable and non-removable media implemented in any method or technology for storage of information such as computer-readable instructions, data structures, program modules or other data. The computer storage media may include, but not limit to, random access memory (RAM), read-only memory (ROM), electrically-erasable programmable read-only memory (EEPROM), flash memory or other memory technology, compact disc read-only memory (CD-ROM), digital versatile disks (DVD) or other optical disk storage, magnetic cassettes, magnetic tape, magnetic disk storage or other magnetic storage devices, or any other medium which can be used to store the desired information and which can be accessed by the computing device 900. The computer storage media may not comprise signals per se.

The communication media typically embodies computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, but not limitation, communication media includes wired media such as a wired network or direct-wired connection, and wireless media such as acoustic, RF, infrared and other wireless media or any combination thereof.

The memory 912 may include computer-storage media in the form of volatile and/or nonvolatile memory. The memory may be removable, non-removable, or a combination thereof. Exemplary hardware devices include solid-state memory, hard drives, optical-disc drives, etc. The computing device 900 includes one or more processors that read data from various entities such as the memory 912 or the I/O components 920. The display component(s) 916 present data indications to a user or to another device. Exemplary presentation components include a display device, speaker, printing component, vibrating component, etc.

The I/O ports 918 allow the computing device 900 to be logically coupled to other devices including the I/O components 920, some of which may be embedded. Illustrative components include a microphone, joystick, game pad, satellite dish, scanner, printer, wireless device, etc. The I/O components 920 may provide a natural user interface (NUI) that processes gestures, voice, or other physiological inputs generated by a user. For example, inputs may be transmitted to an appropriate network element for further processing. A NUI may be implemented to realize speech recognition, touch and stylus recognition, facial recognition, biometric recognition, gesture recognition both on screen and adjacent to the screen, air gestures, head and eye tracking, touch recognition associated with displays on the computing device 900, or any combination thereof. The computing device 900 may be equipped with depth cameras, such as stereoscopic camera systems, infrared camera systems, RGB camera systems, or any combination thereof, to realize gesture detection and recognition. Furthermore, the computing device 900 may be equipped with accelerometers or gyroscopes that enable detection of motion. The output of the accelerometers or gyroscopes may be provided to the display of the computing device 900 to carry out immersive augmented reality or virtual reality.

Furthermore, the processor 914 in the computing device 900 can execute the program code in the memory 912 to perform the above-described actions and steps or other descriptions herein.

It should be understood that any specific order or hierarchy of steps in any disclosed process is an example of a sample approach. Based upon design preferences, it should be understood that the specific order or hierarchy of steps in the processes may be rearranged while remaining within the scope of the present disclosure. The accompanying method claims present elements of the various steps in a sample order, and are not meant to be limited to the specific order or hierarchy presented.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having the same name (but for use of the ordinal term) to distinguish the claim elements.

While the disclosure has been described by way of example and in terms of the preferred embodiments, it should be understood that the disclosure is not limited to the disclosed embodiments. On the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A vehicle warning method based on Vehicle-to-everything (V2X) communication, used in a telematics control unit (TCU) installed in a first vehicle, comprising:

receiving a heartbeat frequency of a user driving the first vehicle;

determining whether the heartbeat frequency is within a normal range;

adding a first loss-of-control flag into a first basic safety message (BSM) when the heartbeat frequency is not within the normal range; and broadcasting the first BSM.

2. The vehicle warning method based on Vehicle-to-everything communication as claimed in claim 1, wherein the first loss-of-control flag is located in a first safety extension frame in the first BSM.

3. The vehicle warning method based on Vehicle-to-everything communication as claimed in claim 1, further comprising:

receiving a second BSM;

determining whether the second BSM comprises a second loss-of-control flag; and transmitting a warning message to notify the user when the second BSM comprises the second loss-of-control flag.

4. The vehicle warning method based on Vehicle-to-everything communication as claimed in claim 3, wherein before transmitting the warning message to notify the user, the method further comprises:

obtaining second vehicle information in the second BSM;

predicting a track of the second vehicle based on the second vehicle information;

determining whether the first vehicle is located in a critical area according to the track; and transmitting the warning message to notify the user when the first vehicle is located in the critical area.

5. The vehicle warning method based on Vehicle-to-everything communication as claimed in claim 4, wherein the second vehicle information at least comprises a position, a speed, a braking state, and a size of the second vehicle.

6. The vehicle warning method based on Vehicle-to-everything communication as claimed in claim 3, wherein the second loss-of-control flag is located in a second safety extension frame in the second BSM.

7. A telematics control unit (TCU) based on Vehicle-to-everything (V2X) communication, installed in a vehicle, comprising:

one or more processors; and one or more non-transitory computer-readable storage media for storing one or more computer-readable instructions, wherein the processor is configured to drive the non-transitory computer-readable storage media to execute the following tasks:

receiving a heartbeat frequency of a user driving the vehicle;

determining whether the heartbeat frequency is within a normal range;

adding a loss-of-control flag into a basic safety message (BSM) when the heartbeat frequency is not within the normal range; and broadcasting the BSM.

8. The telematics control unit based on Vehicle-to-everything (V2X) communication as claimed in claim 7, wherein the loss-of-control flag is located in a safety extension frame in the BSM.

9. A vehicle warning device based on Vehicle-to-everything (V2X) communication, comprising:

one or more processors; and one or more non-transitory computer-readable storage media for storing one or more computer-readable instructions, wherein the processor is configured to drive the non-transitory computer-readable storage media to execute the following tasks:

receiving a basic safety message (BSM);

determining whether the BSM comprises a loss-of-control flag; and transmitting a warning message to notify a user when the BSM comprises the loss-of-control flag.

10. The vehicle warning device based on Vehicle-to-everything communication as claimed in claim 9, wherein before transmitting the warning message to notify the user, the processor further executes the following tasks:

obtaining first vehicle information in the BSM;

predicting a track of the first vehicle according to the first vehicle information;

determining whether the first vehicle is located in a critical area according to the track; and transmitting the warning message to notify the user when the device is located in the critical area.

11. The vehicle warning device based on Vehicle-to-everything communication as claimed in claim 10, wherein the first vehicle information at least comprises a position, a speed, a braking state, and a size of the first vehicle.

12. The vehicle warning device based on Vehicle-to-everything communication as claimed in claim 9, wherein the loss-of-control flag is located in a safety extension frame in the BSM.

13. The vehicle warning device based on Vehicle-to-everything communication as claimed in claim 9, wherein the vehicle warning device is a mobile device.

14. The vehicle warning device based on Vehicle-to-everything communication as claimed in claim 9, wherein the vehicle warning device is a telematics control unit (TCU) installed in a second vehicle.

* * * * *